(12) United States Patent
Krishnan et al.

(10) Patent No.: US 7,713,959 B2
(45) Date of Patent: May 11, 2010

(54) COMPOSITIONS OF AN ANTICONVULSANT AND MIRTAZAPINE TO PREVENT WEIGHT GAIN

(75) Inventors: K. Ranga R. Krishnan, Chapel Hill, NC (US); Kishore M. Gadde, Durham, NC (US)

(73) Assignee: Duke University, Durham, NC (US)

( * ) Notice: Subject to any disclaimer, the term of this patent is extended or adjusted under 35 U.S.C. 154(b) by 883 days.

(21) Appl. No.: 11/216,904

(22) Filed: Aug. 31, 2005

(65) Prior Publication Data

US 2006/0079501 A1    Apr. 13, 2006

Related U.S. Application Data

(63) Continuation-in-part of application No. 11/034,316, filed on Jan. 11, 2005, now Pat. No. 7,429,580.

(60) Provisional application No. 60/616,393, filed on Oct. 5, 2004, provisional application No. 60/567,896, filed on May 3, 2004, provisional application No. 60/535,799, filed on Jan. 13, 2004.

(51) Int. Cl.
| | |
|---|---|
| A61K 9/14 | (2006.01) |
| A61K 31/55 | (2006.01) |
| A61K 31/44 | (2006.01) |
| A61K 31/42 | (2006.01) |
| A61K 31/40 | (2006.01) |
| A61K 31/335 | (2006.01) |
| A61K 31/19 | (2006.01) |
| C07D 223/14 | (2006.01) |
| A01N 43/00 | (2006.01) |
| A01N 43/46 | (2006.01) |
| A01N 43/42 | (2006.01) |
| A01N 43/80 | (2006.01) |
| A01N 43/36 | (2006.01) |
| A01N 43/32 | (2006.01) |
| A01N 47/10 | (2006.01) |
| A01N 37/00 | (2006.01) |

(52) U.S. Cl. .................. 514/214.02; 424/489; 514/217; 514/288; 514/379; 514/424; 514/452; 514/483; 514/557; 540/576

(58) Field of Classification Search ........................ None
See application file for complete search history.

(56) References Cited

U.S. PATENT DOCUMENTS

| | | | |
|---|---|---|---|
| 3,819,706 A | 6/1974 | Mehta | |
| 3,885,046 A | 5/1975 | Mehta | |
| 4,089,855 A | 5/1978 | Chatterjie et al. | |
| 4,172,896 A | 10/1979 | Uno et al. | |
| 4,513,006 A | 4/1985 | Maryanoff et al. | |
| 4,673,679 A | 6/1987 | Aungst et al. | |
| 4,689,332 A | 8/1987 | McLaughlin et al. | |
| 5,202,128 A * | 4/1993 | Morella et al. ............... 424/469 |
| 5,358,970 A | 10/1994 | Ruff et al. | |
| 5,426,112 A | 6/1995 | Zagon et al. | |
| 5,427,798 A | 6/1995 | Ludwig et al. | |
| 5,512,593 A | 4/1996 | Dante | |
| 5,541,231 A | 7/1996 | Ruff et al. | |
| 5,719,197 A | 2/1998 | Kanios et al. | |
| 5,731,000 A | 3/1998 | Ruff et al. | |
| 5,763,493 A | 6/1998 | Ruff et al. | |
| 5,817,665 A | 10/1998 | Dante | |
| 5,856,332 A | 1/1999 | Dante | |
| 5,958,962 A | 9/1999 | Cook | |
| 5,977,099 A * | 11/1999 | Nickolson ............... 514/214.02 |
| 6,004,970 A | 12/1999 | O'Malley et al. | |
| 6,034,091 A | 3/2000 | Dante | |
| 6,071,537 A | 6/2000 | Shank | |
| 6,071,918 A | 6/2000 | Cook | |
| 6,110,973 A | 8/2000 | Young | |
| 6,191,117 B1 | 2/2001 | Kozachuk | |
| 6,262,049 B1 | 7/2001 | Coffin et al. | |
| 6,323,236 B2 | 11/2001 | McElroy | |
| 6,344,474 B1 | 2/2002 | Maruani et al. | |
| 6,437,147 B1 | 8/2002 | Andersen et al. | |
| 6,441,038 B1 | 8/2002 | Cook | |
| 6,506,799 B1 | 1/2003 | Dasseux | |
| 6,541,478 B1 | 4/2003 | O'Malley et al. | |
| 6,548,551 B2 | 4/2003 | Hinz | |

(Continued)

FOREIGN PATENT DOCUMENTS

EP     0 442 769 A2    8/1991

(Continued)

OTHER PUBLICATIONS

McElroy et al. (Biological Psychiatry 2000, 48(6), pp. 539-557).*

(Continued)

*Primary Examiner*—Ernst V Arnold
(74) *Attorney, Agent, or Firm*—Cooley Godward Kronish LLP

(57) ABSTRACT

Disclosed are pharmaceutical compositions comprising mirtazapine and an anticonvulsant drug. Also disclosed are methods of preventing weight gain associated with the administration of mirtazapine comprising identifying a patient to whom mirtazapine is to be administered and administering to said patient a pharmaceutical composition comprising mirtazapine and an anticonvulsant drug. Further disclosed are methods of increasing the efficacy of mirtazapine comprising identifying a patient to whom mirtazapine is to be administered and administering to said patient a pharmaceutical composition comprising mirtazapine and an anticonvulsant drug.

18 Claims, No Drawings

U.S. PATENT DOCUMENTS

| | | | |
|---|---|---|---|
| 6,569,449 | B1 | 5/2003 | Stinchcomb et al. |
| 6,713,488 | B2 | 3/2004 | Sadee et al. |
| 2001/0025038 | A1 | 9/2001 | Coffin et al. |
| 2003/0055008 | A1 | 3/2003 | Marcotte |
| 2003/0109546 | A1 | 6/2003 | Fenton |
| 2003/0144174 | A1 | 7/2003 | Brennan et al. |
| 2004/0002462 | A1 | 1/2004 | Najarian |
| 2004/0029941 | A1 | 2/2004 | Jennings |
| 2004/0033965 | A1 | 2/2004 | Gadde et al. |
| 2004/0092504 | A1* | 5/2004 | Benja-Athon .............. 514/217 |
| 2004/0106576 | A1 | 6/2004 | Jerussi et al. |
| 2004/0122033 | A1 | 6/2004 | Nargund et al. |
| 2004/0198668 | A1 | 10/2004 | Gadde et al. |
| 2004/0254208 | A1 | 12/2004 | Weber et al. |
| 2005/0004106 | A1 | 1/2005 | Romano |
| 2005/0026977 | A1 | 2/2005 | Jennings |
| 2005/0026986 | A1 | 2/2005 | Maruani et al. |
| 2005/0043704 | A1 | 2/2005 | Lieberburg |
| 2005/0043705 | A1 | 2/2005 | Lieberburg |
| 2005/0043773 | A1 | 2/2005 | Lieberburg |
| 2005/0137144 | A1 | 6/2005 | Gadde et al. |
| 2005/0143322 | A1 | 6/2005 | Gadde et al. |
| 2005/0154002 | A1 | 7/2005 | Crooks et al. |
| 2005/0181070 | A1 | 8/2005 | Gadde et al. |
| 2005/0215552 | A1 | 9/2005 | Gadde et al. |
| 2005/0245460 | A1 | 11/2005 | Meyerson et al. |
| 2005/0277579 | A1 | 12/2005 | Krishnano et al. |
| 2006/0009514 | A1 | 1/2006 | Gadde et al. |
| 2006/0058293 | A1 | 3/2006 | Weber et al. |
| 2006/0079501 | A1 | 4/2006 | Krishnan et al. |
| 2006/0100205 | A1 | 5/2006 | Weber et al. |
| 2006/0122127 | A1 | 6/2006 | Rao et al. |
| 2006/0142290 | A1 | 6/2006 | Weber et al. |
| 2006/0160750 | A1 | 7/2006 | Gadde et al. |
| 2006/0276412 | A1 | 12/2006 | Tollefson |

FOREIGN PATENT DOCUMENTS

| | | |
|---|---|---|
| RU | 2214241 | 6/1996 |
| WO | WO 96/09047 | 3/1996 |
| WO | WO 98/00130 | 1/1998 |
| WO | WO 00/50020 | 8/2000 |
| WO | WO 00/76493 | 12/2000 |
| WO | WO 02/09694 | 2/2002 |
| WO | WO 03/013524 | 2/2003 |
| WO | WO 03/092682 | 11/2003 |
| WO | WO 03/097046 | 11/2003 |
| WO | WO 03/097046 A1 | 11/2003 |
| WO | WO 2004/009015 | 1/2004 |
| WO | WO 2004/024096 A2 | 3/2004 |
| WO | WO 2004/096201 | 11/2004 |
| WO | WO 2004/110368 | 12/2004 |
| WO | WO 2004/110375 | 12/2004 |
| WO | WO 2005/000217 | 1/2005 |
| WO | WO 2005/049043 | 6/2005 |
| WO | WO 2005/079773 | 9/2005 |
| WO | WO 2006/017504 | 2/2006 |
| WO | WO 2007/067341 | 6/2007 |
| WO | WO 2007/089318 | 8/2007 |

OTHER PUBLICATIONS

Wheatley et al. (Abstract: J Clin Psychiatry 1998, 59(6), 306-12).*
Sitsen et al. (European Journal of Drug Metabolism and Pharmacokinetics 2001, 26(1-2), 109-121).*
"A Novel Twist on Binge Eating Treatment" Primary Psychiatry; 6(10) 24-29 (1999).
Anderson, et al. Bupropion SR enhances weight loss Obesity R., vol. 10, N. 7, 2002, pp. 633-641, XP002351373.
Altman and Bland. "Standard Deviations and Standard Errors," BMJ; 2005:331:903.
Appolinario et al. "Pharmacological Approaches in the Treatment of Binge Eating Disorder." Current Drug Targets; 5:301-307 (2004).
Asconape. "Some Common Issues in the Use of Antiepileptic Drugs." Seminars in Neurology; 22(1):27-39 (2002).
Atkinson, Clinical Guidelines on the identification, Evaluation, and pharamacologic treatment of obesity in Adults, Online, Jul. 25, 2003, URL:http://www.endotext.org.obesity/obesity15b/obesity15b.htm.
Ayala, "Weight Loss Associated With the Administration of Zonisamide", AES Proceedings, Epilepsia 41(Suppl. 7) :99 (2000)—No. 2.041.
Ayala et al, "Weight Loss Associated With the Administration of Zonisamide", A Compendium of Posters and Platform Sessions for ZONEGRAN™ and DIASTAT®, Presented at the Annual Meeting 2000 of the American Epilepsy Society, Dec. 1-6, 2000, Los Angeles, California.
Beelen, et al. "Asymptomatic QTC prolongation associated with queitiapine fumarate overdose in a patient being treated with risperidone" Human & Experimental Toxicology 92001) 20, 215-219.
Calabrese, et al. Letters to the Editors, "Lamotrigine and Clozapine for Bipolar Disorder" American J. of Psychiatry, vol. 157 Sep. 9, 2000, 1523.
Carlsen, et al. "Evidence for dissociation of insulin-and weight-reducing effects of metformin in non-diabetic male patients with coronary heart disease" Diabetes Research and Clinical Practice Amersterdam, vol. 39, No. 1, Jan. 1998, pp. 47-54.
Carroll, F.I. J. Med. Chem , 46:10 (2003).
Chen, et al. "Synergistic Effects of Cannabiniod inverse agonist AM251 and opiod antagonist namefene on food intake" Brain Res. vol. 999, Jan. 2004, pp. 22-230.
Chengappa, et al. "Changes in body Weight and Body mass index among psychiatric patients receiving lithium, valproate, or topiramate: an open-label, nonrandomized chart review" Clinical Therapeutics, 24 (10) 1576-1584.
Cone, et al. "The arcuate nucleus as a conduit for diverse signals relevant to energy homeostasis,"Int'l Journal of Obesity, 25(5):S63-S67 (2001).
Dechant et al. Drugs, 41:225-253 (1991).
Dembowski, et al. "Successful Antimanic Treatment and Mood Stabilization with Lamotrigine, Clozapine, and Valproate in a Bipolar Patient after Lithium-induced Cerebellar Deterioration" Letter Pharmacopsychiatry, 2003; 36 83-86.
Devlin, et al. Int. J. Eating Disord. 28:325-332 (2000).
Diagnostic and Statistical Manual of Mental Disorders. 4th Edition, Text Revision, p. 583-595 (2000).
Dursen, et al., Clozapine Plus Lamotrigine in Treatment-Resistant Schizophrenia, Arch Gen Psychiatry vol. 56, Oct. 1999, 950-951.
Dursun, et al. "Lamotrgine-Clozapine Combination in Refractory Schizophrenia: Three Cases" J. Neuropsychiatry Clin. Neuroscience, 14:1, Winter 2002, 86.
Dursun, et al. "Augmenting Antipsychotic treatment with Lamotrigine or topiramate in patients with treatment-resistant Schizophrenia: a naturalistic case-series outcome study" Journal of Psychopharmacology 15(4) 2001—297-301.
Dursun, et al., "Psychopharmacology for the Clinician Psychopharmacologie Pratiqu" Journal of Psychiatry Neuroscience, vol. 26 No. 2, 2001, 168.
Dursun, et al. "Accelerated Weight Loss After Treating Refractory Depression with Fluoxetine Puls Topiramate: Possible Mechanism of Action" Canadian Journal of Psychiatry, vol. 46, No. 3 Apr. 2001, pp. 287-288.
Erez et al. J. Med. Chem., 25:847-849 (1982).
Faught et al. "Randomized Controlled Trial of Zonisamide for the Treatment of Refractory Partial-Onset Seizures." Neurology; 57(10):1774-1779 (2001).
Fingl et al. The Pharmacological Basis of Theraputics. Ch.1, pp. 1. (1975).
Fuller et al., Fluoxetine: A Serotonergic Appetite Suppressant Drug, Drug Development Research, vol. 17, No. 1, 1989, pp. 1-15; XP009035038.
Gadde, et al. , "Zonisamide for Weight Loss in Obese Adults—A Randomized Controlled Trial" JAMA 289 (14): 1820-1825 (2003.

Gadde, et al. "Bupropion for Weight Loss: An Investigation of Efficacy and Toleability in Overweight and Obese Women" Obesity Reseach 9 (9): 544:551 (2001).

Gadde et al, "Randomized Controlled Trial of Zonisamide for Treating Obesity", American Epilepsy Society, http://164.109.45.39/submission/aes/status/..\preview.full.asp?presid=2%2E258, Sep. 11, 2002.

Gadde et al, "Randomized Trial of Weight Loss Efficacy of Zonisamide", No. 304, 26(Suppl. 1), Aug. 2002, International Journal of Obesity and Related Metabolic Disorders, Journal of the International Association for the Study of Obesity, Ninth International Congress on Obesity, Sao Paolo, Brazil, Aug. 24-29, 2002 .

Gadde et al, "Zonisamide in Obesity: A 16-Week Randomized Trial", No. NR473, New Research, American Psychiatric Association 2002 Annual Meeting, May 18-23, 2002, Philadelphia, Pennsylvania.

Gadde and Logue, "Bupropion Sustained Release in Obesity: A Randomized Double-Blind, Placebo-Controlled Study", No. NR634, New Research Program & Abstracts, American Psychiatric Association, 1999 Annual Meeting, The Clinician, May 15-20, 1999, Washington, D.C.

Gadde et al. Inpharma; 1383(84):9 (2003).

Gatley, et al. European Journal of Pharmacolgy, 307:331-338 (1996).

Ginsberg and Sussman, "Effects of Mood Stabilizers on Weight", Primary Psychiatry 7(5):49-58 (2000).

Glass et al. Neuropeptides, 33:360-368 (1999).

Grady, "Quest for Weight-Loss Drug Takes an Unusual Turn", The New York Times—Health, www.nytimes.com, Mar. 15, 2003.

Gordon, et al. "Mood Stablization and Weight Loss with Topiramate" American Journal of Psychiatry, American Psychiatric Association, Washington D.C. vol. 156, No. 6, Jun. 1999, pp. 968-969.

Hahn, et al. J. Pharm Exper. Therapeutics 235:846-850.

Harrison's Principles of Internal Medicine. Eleventh Edition, McGraw-Hill Book Company; p. 1921-1930 (1987).

Hussey et al. J. Am. Chem. Soc., 125:3692-3693 (2003).

Islam, et al. Naltrexone, Serotonin Receptor Subtype Antagonists, and Carbohydrate Intake in Rats, Pharmacology Biochemistry and Behavior, vol. 48, No. 1, 1994, pp. 193-201; XP002292383.

Jallon et al. Drug Safety; 24(13):969-978 (2004).

Kiptoo, et al. Enhancement of Transdermal delivery or 6-B-naltrexol via a codrug linked to hydroxyburpropion, Journal of Controlled Release 113 (2006) 137-145.

Kirkham et al. Psychopharmacology 153:267-270(2001).

Tamiz et al. J. Med. Chem., 44:1615:1622 (2001).

Thearle, et al. "Obesity and Pharmacology" Endocrinology and Metabolism Clinics of North American W.B. Suanders Company, Philadelphia US vol. 32, No. 4, pp. 1005-1024. (2003).

Wadden et al. "Effects of Sibutramine Plus Orlistat in Obese Women Following 1 Year of Treatment by Sibutramine Alone: A Placebo-Controlled Trial," Obesity Research; 8(6):431 (2000).

Walker et al, "Chronic Toxicity of the Anticonvulsant Zonisamide in Beagle Dogs", Fundamental and Applied Toxicology 11:333-342 (1988).

Wang, et al., "Gabapentin augmentation therapy in bipolar depression" Bipolar Disorders 2002, 4; 296-301.

Werneke, et al. Options for Pharmacological Management of Obesity in patients Treated with Atypical Antipsychotics, International Clinical Psychopharmacology, vol. 17 No. 4, 2002, pp. 145-160; XP009035036.

Welty et al, "Weight Loss Associated With Use of Zonisamide in European and US Clinical Trials", A Compendium of Posters and Platform Sessions for Zonegran®, Presented at the Annual Meeting 2001 of the American Epilepsy Society, Nov. 30-Dec. 5, 2001, Philadelphia, Pennsylvania.

Wilding. Current Drug Targets; 5:325-332 (2004).

Wilner, "Is Weight Loss With Zonisamide Gender-Specific?", Dr. Tran, 2002 Annual Meeting of the American Epilepsy Society, https://secure.neurohub.net/cgi-perl/get.cgi?pub=52318&ext=htm.

Zeng, et al. Tetrahedron Lett. 29:5123 (1988).

Zhang, et al. "Positional Cloning of the Mouse obese gen and its humane homologue" Nature 372:425-432 (1994).

Zhu, et al. Pharmacologic Treatment of Easting Disorders, Canadian Journal of Psychiatry, vol. 47 No. 3, Apr. 3, 2002 pp. 227-234; XP009035028.

International Search Report and Written Opinion for PCT/US05/00831.

U.S. Appl. No. 11/381,990, filed May 5, 2006, Gadde, et al.

Aronne, et al. "Weight Gain in the Treatment of Mood Disorders"; J Clin Psychiatry 2003;64 (supple 8).

Baldassano et al. Acute treatment of bipolar depression with adjunctive zonisamide: a retrospective chart review. Bipolar Disorders 6:432-434 (2006).

Deshmukh, et al. "Managing weight gain as a side effect of antidepressant therapy"; Cleveland Clinic Journal or Medicine vol. 70, Jul. 7, 2003.

Erfuth, et al. "Bupropion as add-on strategy in difficult-to-treat bipolar depressive patients", Neurophsychobiology, vol. 45, No. Supplement 1, Mar. 2002, pp. 33-36.

Kanba et al., Progress in Neuro-Psychopharmacology and Biological Psychiatry, 18(4), 707-715 (1994).

Kimura, et al. Pharmacokinetic interaction of zonisamide in rats. Effect of other antiepileptics on zonisamide. J. Pharmacobio-Dyn., 15:631-639 (1992).

Kirov, et al. Add-on topiramate reduces weight in overweight patients with affective disorders: a clinical case. BMC Psychiatry, 5:19, 8 pp. (2003).

Kushner, et al. "Obesity pharmacology: past, present, and future.", Current Opinion in Gastroenterology, Mar. 2002, pp. 213-220.

Malhotra, et al., "Medical Management of Obesity Associated With Mental Disorders", Journal or Clinical Psychiatry 2002;63[suppl 4]:24-32.

Penn, et al., "Pharmacotherapy of obesity in the near term.", Current Opinion in Endocrinology and Diabetes 2003 United States, 2003, pp. 311-316.

Potter, et al. "Sustained Weight Loss Associated with 12-month topiramate Therapy" Epilepsia, Raven Press Ltd. New York, vol. 38, No. Suppl 8, 1997, p. 97.

Tollefson, et al., Am J. Psychiatry, 154(5), 457-465 (1997).

Vieta, et al. 1-year follow-up of patients treated with risperidone and topiramate for a manic episode. J Clin Psychiatry 64(7):834-839 (2003).

Vieta, et al. Effects on weight and outcome of long-term olanzapine-topiramate combination treatment in bipolar disorder. Journal of Clinical Psychopharmacology 24(4):374-378 (2004).

McElroy et al.,"Pharmacologic Agents for the Treatment of Acute Bipolar Mania." Biological Psychiatry; 48(6): 539-557 (2000).

Yoshimasu, Kouichi et al., "Psychotropic Drug-Induced Obesity", Nippon Rinsho, 2003, vol. 61, Suppl. 6, pp. 825-829. (English translation of Japanese Office Action containing Examiner's characterization of reference is appended to reference: Notice of Reasons for Rejection, Application No. 2006-549530).

Shriqui, C. L. et al., "Atypical Antipsychotics", The Canadian Journal of CME, Jul. 2002, pp. 65-80.

Restriction Requirement from U.S. Appl. No. 11/034,316, dated Jul. 25, 2006.

Office Action from U.S. Appl. No. 11/034,316, dated Jan. 31, 2007.

Final Office Action from U.S. Appl. No. 11/034,316, dated Jun. 28, 2007.

Office Action from U.S. Appl. No. 11/034,316, dated Sep. 19, 2007.

Office Action from U.S. Appl. No. 11/034,316, dated May 5, 2008.

Restriction Requirement from U.S. Appl. No. 11/242,638, dated Oct. 11, 2007.

* cited by examiner

COMPOSITIONS OF AN ANTICONVULSANT AND MIRTAZAPINE TO PREVENT WEIGHT GAIN

RELATED APPLICATIONS

The present application is a continuation-in-part of U.S. application Ser. No. 11/034,316, filed Jan. 11, 2005, now U.S. Pat. No. 7,429,580 by Gadde et al., and entitled "COMPOSITIONS OF AN ANTICONVULSANT AND AN ANTIPSYCHOTIC DRUG AND METHODS OF USING THE SAME FOR AFFECTING WEIGHT LOSS," which in turn claims priority to U.S. Provisional Patent Application Ser. No. 60/616,393, filed Oct. 5, 2004 by Gadde et al., and entitled "COMPOSITIONS OF AN ANTICONVULSANT AND AN ANTIPSYCHOTIC DRUG AND METHODS OF USING THE SAME FOR AFFECTING WEIGHT LOSS," U.S. Provisional Patent Application Ser. No. 60/567,896, filed May 3, 2004 by Ranga Krishnan, and entitled "COMPOSITIONS FOR AFFECTING WEIGHT LOSS," and U.S. Provisional Patent Application Ser. No. 60/535,799, filed Jan. 13, 2004 by Gadde et al., and entitled "METHOD FOR REDUCING WEIGHT GAIN RISK ASSOCIATED WITH ANTIDEPRESSANT THERAPY," all of which are incorporated herein by reference in their entirety.

BACKGROUND OF THE INVENTION

1. Field of the Invention

The present invention is in the field of pharmaceutical compositions and methods for the treatment of obesity and for affecting weight loss in individuals.

2. Description of the Related Art

Obesity is a disorder characterized by the accumulation of excess fat in the body. Obesity has been recognized as one of the leading causes of disease and is emerging as a global problem. Increased instances of complications such as hypertension, non-insulin dependent diabetes mellitus, arteriosclerosis, dyslipidemia, certain forms of cancer, sleep apnea, and osteoarthritis have been related to increased instances of obesity in the general population.

Obesity has been defined in terms of body mass index (BMI). BMI is calculated as weight (kg)/[height (m)]$^2$. According to the guidelines of the U.S. Centers for Disease Control and Prevention (CDC), and the World Health Organization (WHO) (World Health Organization. Physical status: The use and interpretation of anthropometry. Geneva, Switzerland: World Health Organization 1995. *WHO Technical Report Series*), for adults over 20 years old, BMI falls into one of these categories: below 18.5 is considered underweight, 18.5-24.9 is considered normal, 25.0-29.9 is considered overweight, and 30.0 and above is considered obese.

Prior to 1994, obesity was generally considered a psychological problem. The discovery of the adipostatic hormone leptin in 1994 (Zhang et al., "Positional cloning of the mouse obese gene and its human homologue," Nature 1994; 372: 425-432) brought forth the realization that, in certain cases, obesity may have a biochemical basis. A corollary to this realization was the idea that the treatment of obesity may be achieved by chemical approaches. Since then, a number of such chemical treatments have entered the market. The most famous of these attempts was the introduction of Fen-Phen, a combination of fenfluramine and phentermine. Unfortunately, it was discovered that fenfluramine caused heart-valve complications, which in some cases resulted in the death of the user. Fenfluramine has since been withdrawn from the market. There has been some limited success with other combination therapy approaches, particularly in the field of psychological eating disorders. One such example is Devlin, et al., Int. J. Eating Disord. 28:325-332, 2000, in which a combination of phentermine and fluoxetine showed some efficacy in the treatment of binge eating disorders. Of course, this disorder is an issue for only a small portion of the population.

In addition to those individuals who satisfy a strict definition of medical obesity, a significant portion of the adult population is overweight. These overweight individuals would also benefit from the availability of an effective weight-loss composition. Therefore, there is an unmet need in the art to provide pharmaceutical compositions that can affect weight loss without having other adverse side effects.

SUMMARY OF THE INVENTION

Disclosed are pharmaceutical compositions comprising mirtazapine and an anticonvulsant drug. Also disclosed are methods of preventing weight gain associated with the administration of mirtazapine comprising identifying a patient to whom mirtazapine is to be administered and administering to said patient a pharmaceutical composition comprising mirtazapine and an anticonvulsant drug. Further disclosed are methods of increasing the efficacy of mirtazapine comprising identifying a patient to whom mirtazapine is to be administered and administering to said patient a pharmaceutical composition comprising mirtazapine and an anticonvulsant drug.

DETAILED DESCRIPTION OF THE PREFERRED EMBODIMENT

Newer generation antidepressants seem less likely to be associated with cardiovascular side effects and toxicity associated with older generation antidepressants, such as tricyclic antidepressants or monoamine oxidase inhibitors (MAOIs). Currently, newer generation antidepressants include selective serotonin reuptake inhibitors (e.g., fluoxetine, fluvoxamine, sertraline, paroxetine, citalopram, and escitalopram), venlafaxine, nefazodone, mianserin setiptiline, viqualine trazodone, cianopramine, and mirtazapine. Weight gain has been a major concern with certain of the newer antidepressants, particularly, with paroxetine (PAXIL®) and mirtazapine (Fava, J. Clin. Psych. 61 (suppl. 11):37-41 (2000); Carpenter et al, J. Clin. Psych. 60:45-49 (1999); Aronne et al, J. Clin. Psych. 64 (suppl. 8):22-29 (2003), both of which are incorporated by reference herein in their entirety). A large proportion of patients treated with paroxetine, mirtazapine, and other antidepressants, such as venlafaxine (EFFEXOR®, EFFEXOR XR®), gain a significant amount of weight. Most of these patients find it difficult to lose the weight gained as a result of treatment, even after discontinuing use of the particular antidepressant. Weight gain is unacceptable in patients and a major reason for noncompliance with antidepressant therapy (Cash et al, Percep. Motor Skills 90:453-456 (2000); Deshmukh et al, Cleveland Clinic J. Med. 70:614-618 (2003), both of which are incorporated by reference herein in their entirety). Without being bound by any particular theory, it is believed that potential mechanisms for the observed weight gain include histamine H1 receptor antagonism for mirtazapine, and anticholinergic effects in the case of paroxetine.

Zonisamide is a marketed anticonvulsant indicated as adjunctive therapy for adults with partial onset seizures. Without being bound by any particular theory, it is believed that the mechanism of antiepileptic activity appears to be: 1) sodium-channel blocking; and, 2) reduction of inward T-type calcium currents. In addition, zonisamide binds to the GABA/ benzodiazepine receptor complex without producing change in chloride flux. Further, zonisamide facilitates serotonergic and dopaminergic neurotransmission and possesses a weak inhibitory effect on carbonic anhydrase.

Zonisamide has been shown to cause significant weight loss (comparable to marketed weight loss medications) in patients presenting with primary obesity (Gadde et al, JAMA 289:1820-1825 (2003), incorporated by reference herein in its entirety). It has been postulated that it is the effect of zonisamide on the CNS concentration of serotonin, dopamine and carbonic anhydrase that is responsible for this effect. There is evidence that zonisamide increases serotonin and dopamine synthesis rates (Hashiguti et al, J Neural Transm Gen Sect. 1993;93:213-223; Okada et al, Epilepsy Res. 1992; 13:113-119, both of which are incorporated by reference herein in their entirety). There is further evidence suggesting that zonisamide stimulates dopamine $D_2$ receptors (Okada et al, Epilepsy Res. 1995;22:193-205, incorporated by reference herein in its entirety). Zonisamide was well tolerated, fatigue being the only side effect that occurred more frequently than with placebo treatment.

Thus, the present inventors have determined that the use of anticonvulsants in general is effective in reducing or preventing the weight gain associated with the use of medications such as antidepressants, particularly newer generation of antidepressants, antihistamines, and serotonin receptor antagonists, such as $5HT_{2C}$ receptor antagonists.

Aspects of the present invention provide, at least in part, methods of reducing the risk of weight gain associated with antidepressant therapy. These methods involve the use of weight-loss promoting anticonvulsants. The methods of the present invention are also effective against individuals who have gained weight irrespective of the use of antidepressants.

Thus, in a first aspect, the present invention is directed to a composition for the treatment of obesity or for affecting weight loss comprising a first compound and a second compound, where the first compound is a psychotherapeutic agent and the second compound is an anticonvulsant.

In certain embodiments, the anticonvulsant is effective in reducing convulsions in a mammal. The mammal may be selected from the group consisting of mice, rats, rabbits, guinea pigs, dogs, cats, sheep, goats, cows, primates, such as monkeys, chimpanzees, and apes, and humans.

In some embodiments the psychotherapeutic agent is an antidepressant, an antimigrane, an antibipolar, an antimania drug, a mood stabilizer, or an antiepileptic. Examples of antidepressants include paroxetine and mirtazapine. Examples of antimigrane drugs include sumatriptan, zolmitriptan, elatriptan and other triptans. Examples of antibipolar drugs include lithium, valproate, carbamezepine, oxycarbamezepine, lamotrogine, tiagabine, olanzapine, clozapine, risperidone, quetiapine, aripiprazole, ziprasidone, and benzodiazepines. In a some embodiments, the psychotherapeutic agent comprises a salt of lithium. In other embodiments, the psychotherapeutic agent is valproate, which includes both the salt of valproate and the free acid form of valproic acid. Also included are pharmaceutically acceptable salts or prodrugs of these drugs, extended release formulations of the above drugs, as well as combinations of the above drugs. In some embodiments, the lithium salt may be lithium carbonate or lithium citrate. In some embodiments, the lithium drug is in an extended release formulation.

In some embodiments, the present invention is directed to compositions comprising zonisamide and a salt of lithium, as described herein and in formulations described herein. In other embodiments, the present invention is directed to compositions comprising zonisamide and valproic acid, or a pharmaceutically acceptable salt, such as different salts of valproate, ester, amide, or prodrugs thereof.

In certain embodiments, the antidepressant is a compound of Formula I

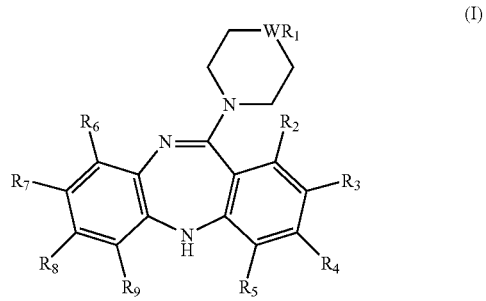

where
W is nitrogen, CH, oxygen, or sulfur;
$R_1$ is selected from the group consisting of hydrogen, optionally substituted $C_{1-6}$ alkyl, optionally substituted $C_{3-8}$ cycloalkyl, optionally substituted $C_{2-6}$ alkenyl, optionally substituted $C_{2-6}$ alkynyl, optionally substituted $C_{1-6}$ alkoxyalkyl, and optionally substituted aryl and arylalkyl;
$R_2$, $R_3$, $R_4$, and $R_5$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, heteroalkyl, and $NO_2$;
$R_6$, $R_7$, $R_8$, and $R_9$, are each independently selected from the group consisting of hydrogen, halogen, optionally substituted $C_{1-6}$ alkyl, optionally substituted $C_{1-6}$ alkyloxy, optionally substituted $C_{2-6}$ alkenyl, optionally substituted $C_{2-6}$ alkynyl, optionally substituted $C_{1-6}$-alkoxyalkyl, optionally substituted $C_{1-6}$ alkylthio, perhaloalkyl, CN, $COR_{10}$, $CONHR_{10}$, heteroalkyl, and $NO_2$.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl) methylamine, and salts thereof with amino acids such as arginine, lysine, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to provide the active moiety.

In another embodiment, the antidepressant is a tricyclic antidepressants. Examples of tricyclic antidepressants include, but are not limited to, imipramine, desipramine, trimipramine, nortriptyline, clomipramine, doxepin, amitriptyline, maprotiline, protriptyline, dothiapen, and maprotiline. Maprotiline, a very effective antidepressant, is not used widely because it carries risk of seizures. The combination of maprotiline and zonisamide or other anticonvulsants has the added benefit of reducing the risk of seizures, in addition to reducing the risk of weight gain due to the use of the antidepressant.

In further embodiments, the antidepressant is a monoamine oxidase inhibitor (MAO inhibitor). Examples of MAO inhibitors include, but are not limited to, phenelzine (Nardil®), tranylcypromine (Parnate®), isocarboxazid (Marplan®) and moclobemide (Aurorix®).

In certain embodiments, the antihistamine is one of setiptilinie, teciptiline, ORG 8282 (Organon, Netherlands), or MO 8282 (Mochida, Japan).

In some embodiments, the $5HT_{2C}$ receptor antagonist is selected from colozapine, N-desmethylclozapine, and clozapine-N-oxide.

In some embodiments, the second compound is an anticonvulsant. Examples of anticonvulsants include barbiturates, benzodiazepines, GABA analogues, hydantoins, miscellaneous anticonvulsants, phenyltriazines, and succinimides. An example of a barbiturate includes pentobarbital. Examples of benzodiazepines include clonazepam, clorazepate, benzodiazepine, and diazepam. Examples of GABA analogues include tiagabine, pregabalin, and gabapentin. Examples of hydantoins include fosphenyloin, phenyloin, and 5,5-Diphenylhydantoin. Examples of miscellaneous anticonvulsants include carbamazepine, valproate, valproic acid, divalproex, felbamate, levetiracetam, carbamazepine, topiramate, oxcarbazepine, and zonisamide. An example of a phenyltriazine is lamotrigine. Examples of succinimides include methsuximide and ethosuximide. Also included are extended release formulations of the above drugs, pharmaceutically acceptable salts or prodrugs thereof, as well as combinations of the above drugs.

In one embodiment, the present invention is directed to a composition for the treatment of obesity or for affecting weight loss comprising zonisamide and mirtazapine. In another embodiment, the present invention is directed to a composition for the treatment of obesity or for affecting weight loss comprising zonisamide and paroxetine. In yet another embodiment, the present invention is directed to a composition for the treatment of obesity or for affecting weight loss comprising zonisamide and venlafaxine.

In certain embodiments, the present invention is directed to a composition for affecting weight loss or for preventing weight gain comprising zonisamide and mirtazapine. In other embodiments, the present invention is directed to a composition for affecting weight loss or for preventing weight gain comprising bupropion and mirtazapine. In further embodiments, the present invention is directed to a composition for affecting weight loss or for preventing weight gain comprising zonisamide and setiptiline. In other embodiments, the present invention is directed to a composition for affecting weight loss or for preventing weight gain comprising bupropion and setiptiline. In additional embodiments, the present invention is directed to a composition for affecting weight loss or for preventing weight gain comprising zonisamide, bupropion, and mirtazapine. In yet other embodiments, the present invention is directed to a composition for affecting weight loss or for preventing weight gain comprising zonisamide, bupropion, and setiptiline.

Throughout the present disclosure, when a particular compound is mentioned by name, for example, zonisamide, bupropion, setiptiline, mirtazapine, or valproate, it is understood that the scope of the present disclosure encompasses pharmaceutically acceptable salts, esters, amides, or prodrugs of the named compound. Also, if the named compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the named compound comprises more than one chiral center, the scope of the present disclosure also includes compositions comprising a mixture of the various diastereomers, as well as compositions comprising each diastereomer substantially free of the other diastereomers. Thus, for example, commercially available mirtazapine is a racemic mixture comprising two separate enantiomers. The recitation of "mirtazapine" throughout this disclosure includes compositions that comprise the racemic mixture of mirtazapine, the compositions that comprise the (+) enantiomer substantially free of the (−) enantiomer, and the compositions that comprise the (−) enantiomer substantially free of the (+) enantiomer.

In another aspect, the present invention is directed to a pharmaceutical composition comprising mirtazapine and an anticonvulsant drug. The anticonvulsant drug may be selected from the group consisting of carbamazepine, valproate, valproic acid, divalproex, felbamate, levetiracetam, carbamazepine, topiramate, oxcarbazepine, and zonisamide. In certain embodiments, the anticonvulsant drug zonisamide.

In some embodiments, the above pharmaceutical composition contains about 15 mg of mirtazapine. In other embodiments, the above pharmaceutical composition contains about 30 mg of mirtazapine. In certain embodiments, the above pharmaceutical composition contains about 100 mg of zonisamide, while in other embodiments, the above pharmaceutical composition contains about 200 mg of zonisamide.

By "about" a certain amount of a drug in a pharmaceutical composition it is meant that the particular drug is present in the pharmaceutical composition to within 20% of enumerated amount. In other embodiments, the particular drug is present in the pharmaceutical composition to within 10% of enumerated amount. In further embodiments, the particular drug is present in the pharmaceutical composition to within 5% of enumerated amount. In yet other embodiments, the particular drug is present in the pharmaceutical composition to within 2% of enumerated amount. Thus, for example, by "about 100 mg of zonisamide" it is meant that the actual amount of zonisamide in the pharmaceutical composition may be 100±20% (that is between 80-120 mg). In other embodiments, it is meant that the actual amount of zonisamide in the pharmaceutical composition may be 100±10% (that is between 90-110 mg). In further embodiments, it is meant that the actual amount of zonisamide in the pharmaceutical composition may be 100±5% (that is between 95-105 mg). In yet other embodiments, it is meant that the actual amount of zonisamide in the pharmaceutical composition may be 100±2% (that is between 98-102 mg).

In another aspect, the present invention relates to a method of preventing weight gain associated with the administration of mirtazapine comprising identifying a patient to whom mirtazapine is to be administered and administering to said patient a pharmaceutical composition comprising mirtazapine and an anticonvulsant drug. In some embodiments, the anticonvulsant drug is selected from the group consisting of carbamazepine, valproate, valproic acid, divalproex, felbamate, levetiracetam, carbamazepine, topiramate, oxcarbazepine, and zonisamide. In further embodiments, the anticonvulsant drug zonisamide.

In some embodiments about 100 mg of zonisamide is administered to said patient, while in other embodiments about 200 mg of zonisamide is administered to said patient.

In yet another aspect, the present invention is related to a method of increasing the efficacy of mirtazapine comprising identifying a patient to whom mirtazapine is to be administered and administering to said patient a pharmaceutical composition comprising mirtazapine and an anticonvulsant drug. In some embodiments, the anticonvulsant drug is selected from the group consisting of carbamazepine, valproate, valproic acid, divalproex, felbamate, levetiracetam, carbamazepine, topiramate, oxcarbazepine, and zonisamide. In further embodiments, the anticonvulsant drug zonisamide.

In some embodiments about 100 mg of zonisamide is administered to said patient, while in other embodiments about 200 mg of zonisamide is administered to said patient.

In some embodiments, the patient has a therapeutically ineffective response to treatment with mirtazapine alone.

Mirtazapine's chemical name is 1,2,3,4,10,14b-hexahydro-2-methylpyrazino [2,1-a]pyrido [2,3-c]benzazepine and its chemical structure is as follows:

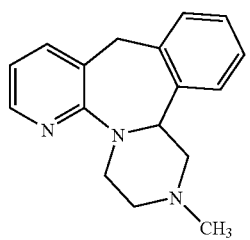

Mirtazapine is useful for the treatment of depression, obstructive sleep apnea/hypopnea syndrome, and other disorders. However, mirtazapine also produces undesirable side effects and symptoms. By "increasing efficacy" it is meant that the usefulness of mirtazapine is increased. For example, 1) certain symptoms that are alleviated by mirtazapine are alleviated to a greater extent when efficacy is increased; 2) certain symptoms that are not alleviated by mirtazapine when used alone are now alleviated when efficacy is increased; or 3) certain side effects or undesirable symptoms caused by mirtazapine are lessened or removed when efficacy is increased.

In some individual patients, administration of mirtazapine alone does not alleviate the symptoms of the underlying disease to the extent that the patient or the attending physician desire. In other individuals, the side effects of mirtazapine are to such extent that treatment with mirtazapine becomes undesirable. In the present disclosure, these individuals are said to show "a therapeutically ineffective response to treatment with mirtazapine alone." Addition of an anticonvulsant, such as those disclosed herein, can increase the efficacy of the mirtazapine to the extent that either the symptoms of the underlying disease are alleviated to the extent that is acceptable to both the patient and the attending physician, or that the extent of undesirable side effects are reduced to the extent that treatment with mirtazapine becomes acceptable.

In another aspect, the present invention relates to a method of affecting weight loss, comprising identifying an individual in need thereof and treating that individual with a psychotherapeutic agent and an anticonvulsant. The psychotherapeutic agent and the anticonvulsant are as described above.

In certain embodiments, the individual has a body mass index (BMI) greater than 25. In other embodiments, the individual has a BMI greater than 30. In still other embodiments, the individual has a BMI greater than 40. However, in some embodiments, the individual may have a BMI less than 25. In some of these embodiments, it may be beneficial for health or cosmetic purposes to affect weight loss, thereby reducing the BMI even further. In some embodiments, the individual has reached the above BMI as the result of antidepressant therapy. In other embodiments, the individual has reached the above BMI without the use of antidepressants.

In some embodiments, the treating step of the above method comprises administering to the individual a first compound and a second compound, where the first compound is a psychotherapeutic agent and the second compound is a anticonvulsant.

In some embodiments the first compound and the second compound are administered more or less simultaneously. In other embodiments the first compound is administered prior to the second compound. In yet other embodiments, the first compound is administered subsequent to the second compound.

In certain embodiments, the first compound and the second compound are administered individually. In other embodiments, the first compound and the second compound are covalently linked to each other such that they form a single chemical entity. The single chemical entity is then digested and is metabolized into two separate physiologically active chemical entities; one of which is the first compound and the other one is the second compound.

In certain embodiments, the first compound is zonisamide and the second compound is mirtazapine. In other embodiments, the first compound is bupropion and the second compound is mirtazapine. In further embodiments, the first compound is zonisamide and the second compound is setiptiline. In other embodiments, the first compound is bupropion and the second compound is setiptiline. In additional embodiments, the first compound is a combination of zonisamide and bupropion and the second compound is mirtazapine. In yet other embodiments, the first compound is a combination of zonisamide and bupropion and the second compound is setiptiline.

In some embodiments, the first compound is zonisamide and the second compound is a salt of lithium, as described herein and in formulations described herein. In other embodiments, the first compound is zonisamide and the second compound is valproic acid, or a pharmaceutically acceptable salt, such as different salts of valproate, ester, amide, or prodrugs thereof.

In some embodiments, the first compound is topiramate and the second compound is a salt of lithium, as described herein and in formulations described herein. In other embodiments, the first compound is topiramate and the second compound is valproic acid, or a pharmaceutically acceptable salt, such as different salts of valproate, ester, amide, or prodrugs thereof.

In another aspect, the present invention relates to a method of increasing satiety in an individual comprising identifying an individual in need thereof and treating that individual with a first compound and a second compound, where the first compound is a psychotherapeutic agent and the second compound is an anticonvulsant.

In some embodiments the first compound and the second compound are administered nearly simultaneously. In other embodiments the first compound is administered prior to the second compound. In yet other embodiments, the first compound is administered subsequent to the second compound.

In yet another aspect, the present invention relates to a method of suppressing the appetite of an individual comprising identifying an individual in need thereof and treating that individual by administering to the individual a first compound and a second compound, where the first compound is a psychotherapeutic agent and the second compound is a anticonvulsant.

In some embodiments the first compound and the second compound are administered nearly simultaneously. In other embodiments the first compound is administered prior to the second compound. In yet other embodiments, the first compound is administered subsequent to the second compound.

In certain embodiments, the first compound is zonisamide and the second compound is mirtazapine. In other embodiments, the first compound is bupropion and the second compound is mirtazapine. In further embodiments, the first compound is zonisamide and the second compound is setiptiline. In other embodiments, the first compound is bupropion and the second compound is setiptiline. In additional embodiments, the first compound is a combination of zonisamide and bupropion and the second compound is mirtazapine. In yet other embodiments, tthe first compound is a combination of zonisamide and bupropion and the second compound is setiptiline.

In another aspect, the present invention relates to a method of increasing energy expenditure in an individual comprising identifying an individual in need thereof and treating that individual by administering to the individual a first compound and a second compound, where the first compound is a psychotherapeutic agent and the second compound is a anticonvulsant.

In some embodiments the first compound and the second compound are administered nearly simultaneously. In other embodiments the first compound is administered prior to the second compound. In yet other embodiments, the first compound is administered subsequent to the second compound.

In certain embodiments disclosed herein, an individual is given a pharmaceutical composition comprising a combination of two or more compounds to affect weight loss. In some of these embodiments, each compound is a separate chemical entity. However, in other embodiments, the two compounds are joined together by a chemical linkage, such as a covalent bond, so that the two different compounds form separate parts of the same molecule. The chemical linkage is selected such that after entry into the body, the linkage is broken, such as by enzymatic action, acid hydrolysis, base hydrolysis, or the like, and the two separate compounds are then formed.

Aspects of the present invention also relate to methods of reducing the risk of weight gain associated with the administration of antidepressants, antihistamines, or serotonin receptor antagonists. Other aspects of the invention further relate to methods of minimizing metabolic risk factors associated with weight gain, such as hypertension, diabetes and dyslipidaemia. In one embodiment, the methods comprise administering to a mammal receiving an antidepressant an amount of zonisamide, or other weight-loss promoting anticonvulsant, sufficient to reduce the weight gain risk associated with the antidepressant. In an alternative embodiment, the methods comprise administering to mammal receiving an antidepressant a combination of zonisamide or topiramate, or other weight-loss promoting anticonvulsant (including agents that block kainate/AMPA (D,L-α-amino-3-hydroxy-5-methyl-isoxazole propionic acid) subtype glutamate receptors), and bupropion, or other compound that enhances the activity of norepinephrine and/or dopamine via uptake inhibition or other mechanism, in an amount sufficient to reduce the weight gain risk associated with the antidepressant.

In certain embodiments, methods of the present invention are directed to reducing the risk of weight gain in an individual who already is on antidepressant therapy, or is about to begin antidepressant therapy. In these embodiments, in addition to the antidepressant, the individual is administered a composition comprising an anticonvulsant and a psychotherapeutic drug, as described herein, where the psychotherapeutic drug is not an antidepressant. Thus, in some embodiments, the individual who is taking mirtazapine or setiptiline is administered a composition comprising zonisamide or a composition comprising zonisamide and bupropion. In other embodiments, the individual who is taking mirtazapine or setiptiline is administered a composition comprising zonisamide or a composition comprising zonisamide and valproate. In further embodiments, the individual who is taking mirtazapine or setiptiline is administered a composition comprising zonisamide or a composition comprising zonisamide and venlafaxine.

In certain embodiments, the weight gain risk-reducing agents for use in the methods of the present invention include zonisamide or topiramate (and pharmaceutically acceptable salts thereof). In other embodiments, other methane-sulfonamide derivatives, such as those described in U.S. Pat. No. 4,172,896, or other sulfamates (including sulfamate-substituted monosaccharides), such as those described in U.S. Pat. No. 4,513,006, incorporated by reference herein in its entirety, are used.

In further embodiments, the weight gain risk-reducing agent is bupropion; while in other embodiments, compounds disclosed in U.S. Pat. Nos. 3,819,706 and 3,885,046, both of which are incorporated by reference herein in their entirety, are used. In additional embodiments, the weight gain risk-reducing agent is a compound that enhances the activity of norepinephrine and/or dopamine, such as by reuptake inhibition or other mechanism. All of the above-mentioned U.S. patents are.

Compounds that enhance the activity of norepinephrine and/or dopamine include norepinephrine agonists, such as phendimetrazine and benzphetamine; norepinephrine reuptake inhibitors such as atomoxetine, bupropion, thionisoxetine, and reboxetine; dopamine agonists, such as cabergoline, amantadine, lisuride, pergolide, ropinirole, pramipexole, and bromocriptine; norepinephrine releasers, for example diethylpropion; a mixed dopamine/norepinephrine reuptake inhibitor, for example, bupropion; a combination of a dopamine reuptake inhibitor and a norepinephrine reuptake inhibitor, e.g. bupropion and mazindol; or a combination of a selective serotonin reuptake inhibitor (SSRI) and a norepinephrine reuptake inhibitor, such as sibutramine, venlafaxine, and duloxetine.

Mammals suitable for treatment in accordance with the instant invention can be receiving any antidepressant associated with weight gain. Typically, however, the antidepressant is a newer generation antidepressant (e.g., a selective serotonin uptake inhibitor (e.g., fluoxetine, fluvoxamine, sertraline, paroxetine, citalopram, and escitalopram), venlafaxine, nefazodone, and mirtazapine)), particularly, paroxetine or mirtazapine.

The amount of weight gain risk-reducing agent(s) administered in the pharmaceutical compositions described herein can vary with the patient, the antidepressant that the patient is receiving, the route of administration and the result sought. Optimum dosing regimens for particular patients can be readily determined by one skilled in the art.

In accordance with the invention, the combination of, for example, zonisamide or topiramate and bupropion (including sustained release preparations) provides an effective means of minimizing metabolic risks associated with weight gain and/or antidepressant use (e.g., type II diabetes). The combination can be more effective than, for example, zonisamide or topiramate treatment alone and with fewer side effects. Neuropharmacologically, all three major nerve transmitters that regulate appetite and weight, i.e., serotonin, norepinephrine and dopamine, are targeted with the combination of, for example, bupropion and zonisamide or topiramate. Side effects of, for example, zonisamide or topiramate (such as somnolence, psychomotor slowing, cognitive impairment, fatigue and depression) can be offset by insomnia, activation, psychomotor agitation and antidepressant effects of, for example, bupropion. On the other hand, zonisamide or topiramate, for example, can reduce the seizure risk associated with, for example, bupropion. Lower doses of both types of medication can be used in the combination treatment, thereby further reducing the overall side effect burden.

With regard to the pharmacokinetics of zonisamide, its renal excretion and minimal potential for inhibition or induction of hepatic microsomal enzymes, are favorable qualities in the concept of combination use with antidepressants, particularly newer generation antidepressants.

In another aspect, the invention relates to a pharmaceutical composition comprising a combination of a psychotherapeutic agent and an anticonvulsant, as described above, or comprising a linked molecule, as described herein, and a physiologically acceptable carrier, diluent, or excipient, or a combination thereof.

Details of some embodiments of the appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein, all of which are incorporated by reference herein in their entirety, including any drawings.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally, including sublingually, which include include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 6000 mg of each ingredient, preferably between 1 mg and 5000 mg, e.g. 25 to 5000 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2500 mg and the total daily dosage by parenteral administration will typically be in the range 0.1 to 400 mg. Suitably the compounds will be administered for a period of continuous therapy, for example for a week or more, or for months or years.

In some embodiments, the dosage range for lithium carbonate, for an oral dose, will result in blood levels of lithium being between about 0.5 and about 1.5 meq/l. In a preferred embodiment, the lithium carbonate dosage range, for an oral dose, will be about 900 mg/day.

In certain embodiments, the dosage range for valproate, for an oral dose, is in the range of about 250 to about 5000 mg/day. In a preferred embodiment, the valproate dosage range, for an oral dose, will be about 1500 mg/day.

In further embodiments, the dosage range for zonisamide, for an oral dose, is in the range of about 25 to about 600 mg per day. In some embodiments, the dosage is 25 mg per day. In other embodiments, the dosage is 50 mg per day. In yet other embodiments, the dosage is 100 mg per day.

In further embodiments, the dosage range for mirtazapine, for an oral dose, is in the range of about 5 to about 500 mg per day. In some embodiments, the dosage is 8 mg per day. In other embodiments, the dosage is 16 mg per day. In yet other embodiments, the dosage is 32 mg per day. In some embodiments, the dosage is 15 mg per day. In other embodiments, the dosage is 30 mg per day. In yet other embodiments, the dosage is 45 mg per day.

In other embodiments, the dosage range for venlafaxin or venlafaxin XR, for an oral dose, is in the range of about 20 mg to about 600 mg per day. In some embodiments, the dosage is 25 mg per day. In other embodiments, the dosage is 37.5 mg per day. In yet other embodiments, the dosage is 50 mg per day. In some embodiments, the dosage is 75 mg per day. In other embodiments, the dosage is 100 mg per day. In yet other embodiments, the dosage is 150 mg per day.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen that maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

It will be understood by those of skill in the art that numerous and various modifications can be made without departing from the spirit of the present invention. Therefore, it should be clearly understood that the forms of the present invention are illustrative only and are not intended to limit the scope of the present invention.

All documents and other information sources cited above are hereby incorporated in their entirety by reference, as are Gadde et al, Obesity Res. 9:544-551 (2001) and Gadde et al, JAMA 289:1820-1825 (2003).

SOME EMBODIMENTS OF THE INVENTION

Some of the embodiments of the present invention are as follows:

In the first embodiment, the invention relates to a composition for affecting weight loss comprising a first compound and a second compound, wherein said first compound is a psychotherapeutic agent and said second compound is an anticonvulsant.

In the second embodiment, the invention relates to the composition of the first embodiment, wherein said psychotherapeutic agent is selected from the group consisting of lithium carbonate, lithium citrate, valproate, mixtures thereof, and pharmaceutically acceptable salts or prodrugs thereof.

In the third embodiment, the invention relates to the composition of the first embodiment, wherein said second compound is selected from the group consisting of a barbiturate, benzodiazepine, GABA analogue, hydantoins, anticonvulsant, phenyltriazine, succinimide, pharmaceutically acceptable salts or prodrugs thereof, and combinations thereof.

In the fourth embodiment, the invention relates to the composition of the third embodiment, wherein said barbiturate is pentobarbital or pharmaceutically acceptable salts or prodrugs thereof.

In the fifth embodiment, the invention relates to the composition of the third embodiment, wherein said benzodiazepine is selected from the group consisting of clonazepam, clorazepate, benzodiazepine, diazepam, pharmaceutically acceptable salts or prodrugs thereof, and combinations thereof.

In the sixth embodiment, the invention relates to the composition of the third embodiment, wherein said GABA analogue is selected from the group consisting of tiagabine, gabapentin, pharmaceutically acceptable salts or prodrugs thereof, and combinations thereof.

In the seventh embodiment, the invention relates to the composition of the third embodiment, wherein said hydantoin is selected from the group consisting of fosphenyloin, phenyloin, 5,5-Diphenylhydantoin, pharmaceutically acceptable salts or prodrugs thereof, and combinations thereof.

In the eighth embodiment, the invention relates to the composition of the third embodiment, wherein said miscellaneous anticonvulsant is selected from the group consisting of carbamazepine, valproate, valproic acid, divalproex, felbamate, levetiracetam, carbamazepine, topiramate, oxcarbazepine, zonisamide, pharmaceutically acceptable salts or prodrugs thereof, and combinations thereof.

In the ninth embodiment, the invention relates to the composition of the third embodiment, wherein said phenyltriazine is lamotrigine.

In the tenth embodiment, the invention relates to the composition of the third embodiment, wherein said succinimide is selected from the group consisting of methsuximide, ethosuximide, and combinations thereof.

In the eleventh embodiment, the invention relates to the composition of the first embodiment, wherein said first compound is a pyschotherapeutic agent and said second compound is a zonisamide.

In the twelfth embodiment, the invention relates to the composition of the first embodiment, wherein said first compound is lithium carbonate or lithium citrate and said second compound is zonisamide.

In the thirteenth embodiment, the invention relates to the composition of the first embodiment, wherein said first compound is valproate and said second compound is zonisamide.

In the fourteenth embodiment, the invention relates to the composition of the twelfth or thirteenth embodiment, wherein the zonisamide is in a time-release formulation.

In the fifteenth embodiment, the invention relates to a method of affecting weight loss, comprising identifying an individual in need thereof and treating that individual with a psychotherapeutic agent and an anticonvulsant.

In the sixteenth embodiment, the invention relates to the method of the fifteenth embodiment, wherein said individual has a body mass index greater than 25.

In the seventeenth embodiment, the invention relates to the method of the fifteenth embodiment, wherein the psychotherapeutic agent is selected from the group consisting of lithium carbonate, lithium citrate, and valproate, extended release formulations of the above drugs, and combinations of the above drugs.

In the eighteenth embodiment, the invention relates to the method of the fifteenth embodiment, wherein the anticonvulsant is selected from the group consisting of barbiturates, benzodiazepines, GABA analogues, hydantoins phenyltriazines, and succinimides, and pharmaceutically acceptable salts or prodrugs thereof.

In the ninteenth embodiment, the invention relates to the method of the fifteenth embodiment, wherein the anticonvulsant is selected from the group consisting of pentobarbital, clonazepam, clorazepate, benzodiazepine, diazepam, tiagabine, gabapentin, pregabalin, fosphenyloin, phenyloin, phenyloin, 5,5-Diphenylhydantoin, carbamazepine, valproate, valproic acid, divalproex, felbamate, levetiracetam, carbamazepine, topiramate, oxcarbazepine, zonisamide, lamotrigine, methsuximide, ethosuximide, extended release formulations of the above drugs, and combinations of the above drugs.

In the twentieth embodiment, the invention relates to the method of the fifteenth embodiment, wherein said first compound and said second compound are administered nearly simultaneously.

In the twenty first embodiment, the invention relates to the method of the fifteenth embodiment, wherein said first compound is administered prior to said second compound.

In the twenty second embodiment, the invention relates to the method of the fifteenth embodiment, wherein said first compound is administered subsequent to said second compound.

In the twenty third embodiment, the invention relates to a method of increasing satiety in an individual comprising identifying an individual in need thereof and treating that individual with a first compound and a second compound, wherein said first compound is a psychotherapeutic agent and said second compound is a anticonvulsant.

In the twenty fourth embodiment, the invention relates to the method of the twenty third embodiment, wherein said first compound and said second compound are administered nearly simultaneously.

In the twenty fifth embodiment, the invention relates to the method of the twenty third embodiment, wherein said first compound is administered prior to said second compound.

In the twenty sixth embodiment, the invention relates to the method of the twenty third embodiment, wherein said first compound is administered subsequent to said second compound.

In the twenty seventh embodiment, the invention relates to a method of increasing energy expenditure in an individual comprising identifying an individual in need thereof and treating that individual with a first compound and a second compound, wherein said first compound is a psychotherapeutic agent and said second compound is an anticonvulsant.

In the twenty eighth embodiment, the invention relates to the method of the twenty seventh embodiment, wherein said first compound and said second compound are administered nearly simultaneously.

In the twenty ninth embodiment, the invention relates to the method of the twenty seventh embodiment, wherein said first compound is administered prior to said second compound.

In the thirtieth embodiment, the invention relates to the method of the twenty seventh embodiment, wherein said first compound is administered subsequent to said second compound.

In the thirty first embodiment, the invention relates to a method of suppressing the appetite of an individual comprising identifying an individual in need thereof and treating that individual with a first compound and a second compound, wherein said first compound is a psychotherapeutic agent and said second compound is an anticonvulsant.

In the thirty second embodiment, the invention relates to the method of the thirty first embodiment, wherein said first compound and said second compound are administered nearly simultaneously.

In the thirty third embodiment, the invention relates to the method of the thirty first embodiment, wherein said first compound is administered prior to said second compound.

In the thirty fourth embodiment, the invention relates to the method of the thirty first embodiment, wherein said first compound is administered subsequent to said second compound.

In the thirty fifth embodiment, the invention relates to a method of affecting weight loss in an individual comprising identifying an individual in need thereof and treating that individual with a combination of lithium carbonate and zonisamide.

In the thirty sixth embodiment, the invention relates to a method of affecting weight loss in an individual comprising identifying an individual in need thereof and treating that individual with a combination of valproate and zonisamide.

In the thirty seventh embodiment, the invention relates to the method of the thirty fifth or thirty sixth embodiments, wherein the individual has a BMI greater than 30.

In the thirty eighth embodiment, the invention relates to the method of the thirty fifth or thirty sixth embodiments, wherein the individual has a BMI greater than 25.

In the thirty ninth embodiment, the invention relates to the method of the thirty fifth or thirty sixth embodiments, wherein the lithium carbonate or valproate is in a time-release formulation.

In the fortieth embodiment, the invention relates to the method of the thirty fifth or thirty sixth embodiments, wherein the plasma concentration level of both the lithium carbonate or valproate and zonisamide follow a similar concentration profile.

In the forty first embodiment, the invention relates to the method of the thirty ninth embodiment, wherein the lithium carbonate or valproate and the zonisamide are administered substantially simultaneously.

In the forty second embodiment, the invention relates to the method of the thirty ninth embodiment, wherein the lithium carbonate or valproate is administered prior to the zonisamide.

In the forty third embodiment, the invention relates to the method of the thirty ninth embodiment, wherein the lithium carbonate or valproate is administered subsequent to the zonisamide.

EXAMPLES

The examples below are non-limiting and are merely representative of various aspects of the invention.

Example 1

Use of Zonisamide Alone

Individuals taking an antidepressant, or about to take an antidepressant, who have gained weight as the result of the use of the antidepressant, or are susceptible to gain weight as the result of the use of the antidepressant, are identified. Each individual is instructed to take one 25 mg tablet of zonisamide on a daily basis, in addition to the antidepressant therapy.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

The dosage of zonisamide can be from about 25 mg to about 800 mg per day, generally given once per day or divided (e.g., equally) into multiple doses. Preferably, the dose is from about 100 mg to about 600 mg per day, more preferably, the dose is from about 200 mg to about 400 mg per day. However, it may be necessary to use dosages outside these ranges. Zonisamide tablets are usually made and marketed in 25 mg, 50 mg, and 100 mg doses. Individual tablets, or combination of tablets can be used to achieve the desired dosing.

Example 2

Use of Topiramate Alone

Individuals taking an antidepressant, or about to take an antidepressant, who have gained weight as the result of the use of the antidepressant, or are susceptible to gain weight as the result of the use of the antidepressant, are identified. Each individual is instructed to take one 25 mg tablet of topiramate on a daily basis, in addition to the antidepressant therapy.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

The dosage of topiramate can be from about 25 mg to about 1600 mg, preferably from about 50 mg to about 600 mg, more preferably from about 100 mg to about 400 mg. However, it may be necessary to use dosages outside these ranges.

Example 3

Combination of Zonisamide and Mirtazapine

Individuals having a BMI of greater than 25 are identified. Each individual is instructed to take one tablet of zonisamide on a daily basis, in addition to one tablet of mirtazapine on a daily basis. Initially, the drugs are administered as follows: 8 mg mirtazapine and 64 mg zonisamide; or 16 mg mirtazapine and 128 mg zonisamide; or 32 mg mirtazapine and 252 mg zonisamide; generally with an mirtazapine/zonisamide ratio of 1:8.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosages are not effective, they can be increased.

Example 4

Combination of Zonisamide and Paroxetine

Individuals having a BMI of greater than 25 are identified. Each individual is instructed to take one tablet of zonisamide on a daily basis, in addition to one tablet of paroxetine on a daily basis. Initially, the drugs are administered as follows: 10 mg paroxetine and 60 mg zonisamide; or 20 mg paroxetine and 120 mg zonisamide; or 30 mg paroxetine and 180 mg zonisamide; or 40 mg paroxetine and 240 mg zonisamide; generally with a paroxetine/zonisamide ratio of 1:6.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosages are not effective, they can be increased.

Example 5

Combination of Zonisamide and Lithium Carbonate

Individuals having a BMI of greater than 25 are identified. Each individual is instructed to take one 25 mg tablet of zonisamide on a daily basis, in addition to one 300 mg tablet of lithium carbonate on a daily basis.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the zonisamide dosage can be increased by approximately 25 mg per day. If the initial dosage results in a more rapid weight loss than the above rate, the dosage of each of zonisamide or lithium carbonate can be reduced.

In some cases, it is beneficial to administer one dose of zonisamide per day in conjunction with two or three or more doses of lithium carbonate throughout the day. Lithium carbonate may also be in a time-release formulation where the dose is administered once a day, but lithium carbonate gradually enters the blood stream throughout the day, or in the course of a 12 hour period.

The above procedure can be followed using lithium citrate, or any other pharmaceutically acceptable salt of lithium, instead of lithium carbonate.

Example 6

Combination of Zonisamide and Lithium Carbonate

Individuals having a BMI of greater than 25 are identified. Each individual is instructed to take one 25 mg tablet of zonisamide on a daily basis. In addition, each individual is instructed to take one 300 mg tablet of lithium carbonate on a daily basis.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs. It is recommended that serum creatinine be checked periodically.

If the initial dosage is not effective, then the lithium carbonate dosage can be increased so as to achieve blood levels of 0.5 to 1.5 meq/l. If the initial dosage results in a more rapid weight loss than the above rate, the dosage of each of zonisamide or lithium carbonate can be reduced.

The above procedure can be followed using lithium citrate, or any other pharmaceutically acceptable salt of lithium, instead of lithium carbonate.

Example 7

Combination of Zonisamide and Valtproate

Individuals having a BMI of greater than 25 are identified. Each individual is instructed to take one 50 mg tablet of zonisamide on a daily basis, in addition to one 500 mg tablet of valproate on a daily basis.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the zonisamide dosage can be increased by approximately 30 mg per day, though not exceeding 600 mg total per day. If the initial dosage results in a more rapid weight loss than the above rate, the dosage of each of zonisamide or valproate can be reduced.

In some cases, it is beneficial to administer one dose of zonisamide per day in conjunction with two or three or more doses of valproate throughout the day. Valproate may also be in a time-release formulation where the dose is administered once a day, but valproate gradually enters the blood stream throughout the day, or in the course of a 12 hour period.

Example 8

Combination of Zonisamide and Valproate

Individuals having a BMI of greater than 25 are identified. Each individual is instructed to take one 50 mg tablet of zonisamide on a daily basis. In addition, each individual is instructed to take one 250 mg tablet of valproate on a daily basis.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the valproate dosage can be increased by 20 mg intervals up to 3000 mg per day. If the initial dosage results in a more rapid weight loss than the above rate, the dosage of each of zonisamide or valproate can be reduced.

Example 9

Zonisamide and/or Bupropion Prevent the Weight Gain Associated with Mirtazapine or Setiptiline Treatment Background Mirtazapine shows considerable promise as a therapy for sleep apnea, but it causes weight gain in some patients. This weight gain limits the use of mirtazapine as a therapy for sleep apnea or as an antidepressant. Addition of zonisamide, or bupropion, or zonisamide plus bupropion, to concomitant mirtazapine treatment decreases the weight gain associated with mirtazapine, in a rodent model of mirtazapine-induced weight gain.

The melanocortin system controls energy balance. Mirtazapine and setiptiline change the activity of melanocortin circuits. Zonisamide, or bupropion, or zonisamide plus bupropion reverse this change in neuronal activity.

The melanocortin system consists of Proopiomelanocortin (POMC) neurons, the cognate melanocortin receptors (MC4 R) and the agouti-related peptide neurons in the arcuate nucleus of the hypothalamus. It is well established in humans and animals that the melanocortin system controls energy balance and the most common genetic cause of obesity in humans is congenital lack of MC4 R.

It has recently been shown that many compounds that influence energy balance modify the activity of melanocortin circuits. In particular, it has been shown that bupropion and zonisamide increase the electrophysiological activity of POMC neurons. As part of this research some of the receptors that can regulate the activity of POMC neurons have been identified; specifically it has been shown that 5-HT 2C and 5-HT 1B receptors increase the activity of POMC neurons as does dopamine D2 R. The clear role of 5-HT 2CR in regulating the activity of POMC neurons suggests that compounds like mirtazapine, which is an antagonist at this receptor, modify energy balance to induce an anabolic state, favoring weight gain.

In Vivo Pharmacology

We have developed a model to pre-clinically test the effects of mirtazapine on body weight gain. Dose-ranging studies are performed to determine the dose that best demonstrates the weight gain caused by mirtazapine or by setiptiline in the "rat-weight gain assay". Zonisamide, or bupropion, or zonisamide plus bupropion are tested to decrease the weight gain seen in response to concomitant mirtazapine or setiptiline therapy.

In a 4×3 design rats receive implants that secrete mirtazapine, or setiptiline, or vehicle. Some rats also receive co-treatment with saline, some receive zonisamide, some receive bupropion, and others receive co-treatment with zonisamide plus bupropion. In this way cohorts of 10 rats receive all possible combinations of the weight loss drug(s) with mirtazapine or setiptiline.

| | Rat numbers and groups | | |
|---|---|---|---|
| Weight loss agent | Vehicle | Setiptiline (tbd) | Mirtazapine (tbd) |
| Vehicle | 10 | 10 | 10 |
| Zonisamide (tbd) | 10 | 10 | 10 |
| Bupropion (tbd) | 10 | 10 | 10 |
| Zonisamide (tbd) + Bupropion (tbd) | 10 | 10 | 10 |

Electrophysiology

The electrophysiological response of POMC neurons to mirtazapine and to setiptiline is determined. It is then determined if co-treatment with zonisamide, or bupropion, or zonisamide plus bupropion prevents the expected decrease in POMC activity due to mirtazapine or setiptiline.

Preliminary data show that sub-threshold doses of zonisamide and bupropion synergistically inhibit acute food intake in mice, which is further evidence of powerful synergy between zonisamide and bupropion to inhibit food intake in mice after a 16 hr fast.

In other preclinical experiments it has been shown that zonisamide and bupropion each inhibit food intake. These effects had faded by 4 hours, but the combination was effective when each compound alone was ineffective. The weight reducing effects of zonisamide and bupropion have also been well demonstrated in humans (Gadde et al, 2003; Gadde et al, 2001).

It has also been shown that zonisamide in combination with bupropion strongly increases the electrophysiological activity of POMC neurons in brain slices from POMC-EGFP mice. It has been shown that a large increase in rate of spontaneous action potentials in POMC neurons would be expected to stimulate significant secretion of α-MSH from POMC neurons, and consequent activation of MC4 R—to inhibit food intake and decrease body weight gain.

Procedures

In Vivo Pharmacology

Female Sprague-Dawley rats weighing about 300 grams at the start of the experiment are used. Under isoflurane anesthesia, Alzet osmotic minipumps (2 ml2) are implanted subcutaneously between the shoulder blades. The rats are returned to their home cages after recovery. The minipumps deliver 5 μL per hour for 14 days. A range of doses of mirtazapine (from 0.1 to 20 mg/kg/day dissolved in DMSO/saline) are used. Animals are housed individually and supplied with standard laboratory chow. Food consumed and animal weights are recorded every 3 days, to minimize disruption of the animals.

We have already shown in mice that bupropion, zonisamide, and zonisamide plus bupropion have pronounced effects on food intake after intra-peritoneal injection. We will develop chronic infusion methods to test the effects of bupropion, or zonisamide and zonisamide plus bupropion on weight gain over 14 days using the following groups:

7 groups of 6 rats (6 doses of mirtazapine (0.1, 0.5, 1, 5, 10, 20 mg/kg), +saline)

The doses of zonisamide, and bupropion, and zonisamide plus bupropion that cause weight loss in this rat model in the preliminary studies are determined; the co-treatment experiments (mirtazapine plus zonisamide plus bupropion) are then performed.

Electrophysiology

The electrophysiological activity of Proopiomelanocortin (POMC) neurons in brain slices from POMC-EGFP mice are recorded. The POMC neurons in these mice are identified by the expression of green fluorescent protein (EGFP) in these, and only these, cells. The frequency of action potentials in these neurons are recorded using standard electrophysiological techniques. In particular loose cell attached patch configuration is used to determine action potential frequency, whilst minimally disturbing the cells.

It has been shown that zonisamide, or bupropion, or zonisamide plus bupropion increase the activity of POMC neurons. The basal activity is recorded, and then mirtazapine or setiptiline is added to the tissue bath to determine the effect of the antidepressant on the activity of POMC neurons. If mirtazapine or setiptiline inhibits the activity of POMC neurons, the increase in neuronal activity by treating the brain slices with bupropion, or zonisamide or zonisamide plus bupropion is tested.

Example 18

Combination of Zonisamide and Mirtazapine

Mirtazapine use has been associated with increases in appetite and body weight. In US controlled studies, appetite increase was reported in 17% of patients treated with mirtazapine, compared to 2% for placebo and 6% for amitriptyline. In these same trials, weight gain of ≧7% of body weight was reported in 7.5% of patients treated with mirtazapine, compared to 0% for placebo and 5.9% for amitriptyline. In a pool of premarketing US studies, including many patients for long-term, open label treatment, 8% of patients receiving mirtazapine discontinued for weight gain. Other studies report a higher incidence of weight gain (75% of mirtazapine-treated patients experienced weight gain averaging 1.5 kg) during the first 4 weeks of therapy (Goodnick et al., 1999, Prim. Psychiatry, 6:103-108). Weight gain was greater among patients with a lower BMI (<25) at baseline than among those with a higher BMI (>30).

The long-term effects of mirtazapine on body weight have been investigated in a relapse prevention study in depression; 410 patients received open label treatment with mirtazapine or placebo for 8-12 weeks after which the responders were randomized to receive double-blind treatment with mirtazapine or placebo for 40 weeks (Thase et al., 1999, Eur. Neuropsychopharm, 10 (suppl 3):S265-S266). In the open label phase, mirtazapine treatment resulted in a mean increase in body weight of 2.5 kg. However, during the long-term, double-blind phase, the mean weight increase with mirtazapine (3.3 kg) was only slightly greater than with placebo (2.7 kg). Therefore, it is possible that body weight changes induced by mirtazapine are transient and apparent only during initial phases of treatment.

In this study, the ability of zonisamide to prevent the increase in body weight associated with mirtazapine is assessed. Effectiveness measures include minimizing weight gain Efficacy is assessed using a number of outcome measures including change in Craving Scale for Australia and change in weight.

The study is a single-blind, multi-centre proof of concept trial conducted at 4 study centers in Sydney, Australia. Eighty patients at four study sites are randomized and complete this study. Patients who terminate from the trial early are replaced. There are three groups to which patients are assigned based on a 2:1:1 ratio. The duration of treatment and study participation lasts approximately four weeks. Patients are assigned to one of the following treatment groups based on timing of their baseline visit.

group 1: mirtazapine 15 mg po nocte+placebo po nocte
group 2: mirtazapine 15 mg po nocte+100 mg zonisamide po nocte
group 3: placebo po nocte+placebo po nocte The results show that patients in group 2 did not gain as much weight, if any at all, compared to patients in group 1. In fact, the results show that there was no significant weight gain or loss between the patients in group 2 and the patients in group 3. In particular, the results show that patients in group 2 had no appreciable weight gain as compared to patients in group 1. Therefore, the results show that addition of 100 mg of zonisamide to a treatment regimen of 15 mg of mirtazapine reduced or stopped the weight gain associated with mirtazapine therapy.

Example 19

Combination of Zonisamide and Mirtazapine

The example is directed to assessing the ability of zonisamide to minimize weight gain in patients treated with mirtazapine. Efficacy is assessed using a number of outcome measures including change in Craving Scale for Australia and change in weight.

This is a single-blind, multi-centre proof of concept trial conducted at four investigative sites within Australia. One hundred patients at 4 study sites are randomized and complete this study. Patients who terminate from the trial early are replaced. There are five groups to which patients are assigned based on a 1:1:1:1:1 ratio. The duration of treatment and study participation lasts approximately four weeks. Patients are assigned to one of the following treatment groups based on timing of their baseline visit.

group 1: placebo+100 mg zonisamide, weeks 1/2; placebo+200 mg zonisamide, weeks 3/4
group 2: 15 mg mirtazapine+100 mg zonisamide, weeks 1/2; 15 mg mirtazapine+200 mg zonisamide, weeks 3/4
group 3: 30 mg mirtazapine+100 mg zonisamide, weeks 1/2; 30 mg mirtazapine+200 mg zonisamide, weeks 3/4
group 4: 30 mg mirtazapine+placebo
group 5: placebo The results show that patients in groups 2 and 3 did not gain as much weight, if any at all, compared to patients in group 4. In fact, the results show that there was no significant weight gain or loss between the patients in group 2 or 3 and the patients in group 5.

What is claimed is:

1. A pharmaceutical composition comprising mirtazapine or a pharmaceutically acceptable salt thereof and an effective amount of an anticonvulsant drug or a pharmaceutically acceptable salt thereof, wherein the anticonvulsant drug is selected from the group consisting of valproate, valproic acid, divalproex, felbamate, levetiracetam, topiramate, oxcarbazepine, zonisamide and pharmaceutically acceptable salts thereof; and the pharmaceutical composition is in a single oral dosage form.

2. The pharmaceutical composition of claim 1, wherein said anticonvulsant drug is zonisamide or a pharmaceutically acceptable salt thereof.

3. The pharmaceutical composition of claim 1, further comprising a pharmaceutically acceptable carrier, diluent, or excipient.

4. The pharmaceutical composition of claim 1, wherein the pharmaceutical composition contains about 15 mg of mirtazapine or a pharmaceutically acceptable salt thereof.

5. The pharmaceutical composition of claim 1, wherein the pharmaceutical composition contains about 30 mg of mirtazapine or a pharmaceutically acceptable salt thereof.

6. The pharmaceutical composition of claim 2, wherein the pharmaceutical composition contains about 100 mg of zonisamide or a pharmaceutically acceptable salt thereof.

7. The pharmaceutical composition of claim 2, wherein the pharmaceutical composition contains about 200 mg of zonisamide or a pharmaceutically acceptable salt thereof.

8. The pharmaceutical composition of claim 2, wherein said composition comprises from about 25 mg to about 600 mg of said zonisamide or pharmaceutically acceptable salt thereof.

9. The pharmaceutical composition of claim 2, wherein said composition comprises from about 5 mg to about 500 mg of said mirtazapine or pharmaceutically acceptable salt thereof.

10. The pharmaceutical composition of claim 8, wherein said composition comprises from about 5 mg to about 500 mg of said mirtazapine or pharmaceutically acceptable salt thereof.

11. The pharmaceutical composition of claim 2, wherein said composition comprises an amount of said zonisamide or pharmaceutically acceptable salt thereof selected from the group consisting of 25 mg, 50 mg, 64 mg, 100 mg, 128 mg, 200 mg and 252 mg.

12. The pharmaceutical composition of claim 2, wherein said composition comprises an amount of said mirtazapine or pharmaceutically acceptable salt thereof selected from the group consisting of 8 mg, 15 mg, 16 mg, 30 mg, 32 mg, and 45 mg.

13. The pharmaceutical composition of claim 11, wherein said composition comprises an amount of said mirtazapine or pharmaceutically acceptable salt thereof selected from the group consisting of 8 mg, 15 mg, 16 mg, 30 mg, 32 mg, and 45 mg.

14. The pharmaceutical composition of claim 2, wherein said zonisamide or pharmaceutically acceptable salt thereof is a sustained release formulation.

15. The pharmaceutical composition of claim 8, wherein said zonisamide or pharmaceutically acceptable salt thereof is a sustained release formulation.

16. The pharmaceutical composition of claim 10, wherein said zonisamide or pharmaceutically acceptable salt thereof is a sustained release formulation.

17. The pharmaceutical composition of claim 11, wherein said zonisamide or pharmaceutically acceptable salt thereof is a sustained release formulation.

18. The pharmaceutical composition of claim 13, wherein said zonisamide or pharmaceutically acceptable salt thereof is a sustained release formulation.

\* \* \* \* \*